United States Patent
Willcut et al.

(10) Patent No.: US 10,315,051 B2
(45) Date of Patent: *Jun. 11, 2019

(54) COLLIMATOR FOR RADIOTHERAPY APPARATUS

(71) Applicant: ELEKTA AB (PUBL), Stockholm (SE)

(72) Inventors: Virgil Willcut, Kirkwood, MO (US); Martin Broad, Bromley Kent (GB); David Anthony Roberts, East Grinstead (GB)

(73) Assignee: ELEKTA AB (PUBL), Stockholm (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/725,784

(22) Filed: Oct. 5, 2017

(65) Prior Publication Data
US 2018/0043186 A1    Feb. 15, 2018

Related U.S. Application Data

(63) Continuation of application No. 15/394,193, filed on Dec. 29, 2016, now Pat. No. 9,808,652, which is a continuation of application No. 14/495,137, filed on Sep. 24, 2014, now Pat. No. 9,572,998.

(30) Foreign Application Priority Data

Sep. 25, 2013   (GB) ................................. 1317016.2
Jun. 20, 2014   (GB) ................................. 141105.0

(51) Int. Cl.
| | |
|---|---|
| *A61N 5/10* | (2006.01) |
| *G21K 1/04* | (2006.01) |
| *G21K 1/10* | (2006.01) |
| *G21K 1/02* | (2006.01) |

(52) U.S. Cl.
CPC ......... *A61N 5/1045* (2013.01); *A61N 5/1077* (2013.01); *G21K 1/025* (2013.01); *G21K 1/046* (2013.01); *G21K 1/10* (2013.01)

(58) Field of Classification Search
CPC .............................. A61N 5/1045; G21K 1/046
See application file for complete search history.

(56) References Cited

U.S. PATENT DOCUMENTS

| | | | |
|---|---|---|---|
| 4,472,637 | A | 9/1984 | Sportelli |
| 5,115,139 | A | 5/1992 | Cotter |
| 6,148,062 | A | 11/2000 | Romeas |

(Continued)

FOREIGN PATENT DOCUMENTS

| | | |
|---|---|---|
| EP | 0 314 214 A2 | 5/1989 |
| EP | 2 153 448 B1 | 7/2012 |

OTHER PUBLICATIONS

Intellectual Property Search Report from the Intellectual Property Patent Office, dated Feb. 26, 2014, in corresponding Application No. GB 1317016.2, 1 page.

*Primary Examiner* — Thomas R Artman
(74) *Attorney, Agent, or Firm* — Finnegan, Henderson, Farabow, Garrett & Dunner LLP

(57) ABSTRACT

A collimator for a radiotherapy apparatus, comprising a block of isolation-attenuating material having a front face forming the leading edge of tie block and at least one main rear face defining the trailing edge of the block, in which the or each rear face is substantially planar in the direction of the depth of the block and non-parallel to the front face. The collimator may form part of a radiotherapy apparatus, and methods of operation of such apparatus are described.

19 Claims, 3 Drawing Sheets

(56) References Cited

U.S. PATENT DOCUMENTS

| | | |
|---|---|---|
| 7,085,355 B1 | 8/2006 | Albagli et al. |
| 8,816,307 B2 | 8/2014 | Kuusela et al. |
| 2006/0045238 A1 | 3/2006 | Nguyen |
| 2012/0012763 A1 | 1/2012 | Kuusela et al. |

COLLIMATOR FOR RADIOTHERAPY APPARATUS

CROSS REFERENCE TO RELATED APPLICATIONS

This is a continuation of application Ser. No. 15/394,193, filed Dec. 29, 2016, which claims the benefit of application Ser. No. 14/495,137, filed Sep. 24, 2014, and GB 1317016.2, filed Sep. 25, 2013, and GB 1411005.0, filed Jun. 20, 2014, all of which are expressly incorporated herein by reference in their entirety.

FIELD OF THE INVENTION

The present invention relates to a collimator, particularly but not exclusively to a collimator for radiotherapy apparatus.

BACKGROUND ART

Radiotherapy is a form of treatment for tumours and other lesions which involves directing a beam of ionising radiation toward the lesion. The radiation harms the tumour tissue and causes its reduction or elimination. However, the radiation is also harmful to healthy tissue around the lesion; although healthy tissue is slightly less susceptible to the effects of ionising radiation, measures are taken to limit the exposure of healthy tissue to the extent possible.

One such measure is to direct the beam toward the lesion from a number of radial directions by mounting the radiation source in a treatment head which is movable with respect to the lesion, such as by being mounted on a rotatable gantry. Thus, the lesion (or part of it) remains in the beam at substantially all times whereas each individual section of healthy tissue around the beam is only exposed to the beam briefly. In this way, the dose delivered to the lesion can be a multiple of the dose delivered to healthy tissue remote from the lesion.

Another measure is to collimate the beam so as to limit its lateral extent and avoid the unnecessary irradiation of healthy tissue. Modern collimators for radiotherapy devices are known as "multi-leaf collimators" and comprise an array of adjacent tungsten leaves, each of which is narrow so as to provide a high resolution but deep (in the direction of the beam) so as to provide an effective attenuation of the beam. Each leaf is moveable into and out of the beam, largely independently of those around it, so that the tips of the individual leaves can define a variable shape as required. Two such "banks" of leaves will usually be provided, on opposing sides of the beam aperture, thereby allowing a field to be defined within that aperture, of substantially any shape. An example of a multi-leaf collimator (MLC) is disclosed in our earlier application published as EP-A-0314214.

There are however limits to the attenuation that can be provided by a multi-leaf collimator. In particular, rules govern the minimum distance between opposing leaves so as to prevent the leaves from jamming or being damaged. Further, whilst it may be permissible for one leaf to be extended so that its tip touches or very closely approaches the tip of the exactly opposite leaf, those tips are usually rounded so as to provide a small penumbra at the patient, and therefore there will be leakage from the gap between them. For these reasons, there is usually a "block collimator" in series with the multi-leaf collimator, in the form of a substantial block of tungsten that can be extended or retracted in a direction transverse to the movement direction of the leaves. Thus, it can cover a region outside the defined field where the entire width of the aperture needs to be covered. Typically, there will be a pair of block collimators, one either side of the beam, the or each block collimator being substantially square or rectangular, as seen in the direction of the radiation beam to be collimated.

The block does impose a substantial weight penalty. The collimators are usually accommodated in the radiation source, which is to be rotated around the patient in order to allow the beam to be directed toward the lesion from a variety of radial directions. Thus, a reduction in this weight would be beneficial. Our earlier application EP2153448A1 described one such way of doing so.

The collimator blocks are required to be of the order of 8 cm thick solid tungsten material. This imposes a significant weight burden. Correspondingly, the mechanism required to move a significantly greater mass of collimator block will be correspondingly heavier itself. Both of these increase the overall mass of the treatment head, which in turn causes the structure of the radiotherapy apparatus to deflect more, resulting in further complications for the compensating control systems. It should be borne in mind that most clinical accelerators place the treatment head at the end of a long arm which is mounted on a rotatable support so that the treatment head can be rotated around the patient. Additional mass at the end of that arm causes the arm to deform in a direction which will vary (relative to the treatment head) as the treatment head traverses in an arc around the patient. The present invention therefore seeks to provide an arrangement which is able to offer the necessary blocking of the radiation beam, whilst reducing mass over conventional arrangements.

SUMMARY OF THE INVENTION

The present invention provides a collimator for a radiotherapy apparatus, comprising a block of radiation-attenuating material for moving into and out of a beam of therapeutic radiation having a depth and a front face forming the leading edge of the block when, in use, it is moved into the beam and one, two or more main rear faces opposite the front face which main rear face(s) together substantially define(s) the trailing edge of the block when, in use, it is moved into the beam, the or each main rear face being substantially planar in the direction of the depth of the block and non-parallel to the front face. Such an arrangement enables the size and therefore weight of the collimator to be reduced as compared to conventional block collimators, as will be further described below.

There may be a single rear face, or there may be two rear faces which together form a concave V-shape in the block opposite the front face. The or each rear face is substantially planar and non-parallel to the front face. These arrangements are both simple and enable significant savings in block material and hence weight to be made; single rear face, or "wedge" embodiments, enable greater weight savings than similar implementations having two rear faces (or concave V-shaped embodiments), as will be explained below. Embodiments having three or more rear faces in a concave shape are technically feasible, but these are more complex to manufacture and provide little additional benefit in weight saving.

The angle between the or each rear face and the front face is suitably determined so as to match the trajectory the leaves of an MLC take as they move between extremes of positioning with the trajectory of the collimator block, which is dependent on the speeds of movement of the MLC leaves and the collimator block; accordingly, this angle may be between 10 and 80 degrees, and may be between 30 and 60 degrees.

There may be two side faces leading from the front face to the rear face (where there is only one rear face); this provides a safety margin when movement of the block collimator and MLC leaves is initiated. The side faces may be substantially parallel.

The collimator may have a top and bottom face (as seen in the direction of the radiation beam which is collimated), and these faces may be planar; to the extent that they are planar these faces may be substantially parallel. Additionally or alternatively, these faces may be shaped as described in our EP2153448A1, so as to provide additional weight saving; in particular the edge of the collimator block at its front face (the front edge) may be of greater thickness than at least one region behind the front edge (i.e. towards the rear face(s)), between the leading and trailing edges of the block.

It is envisaged that the collimator blocks may be mountable in a radiotherapy apparatus so that they may be moved back and forth in a direction transverse to the front face. The collimator blocks may be shaped and configured so as to be moveable through an arc centred on the nominal point source of the radiation beam, as is known in the art.

In other aspects, the invention also provides radiotherapy apparatus including such collimators, and methods of operating such radiotherapy apparatus.

BRIEF DESCRIPTION OF THE DRAWINGS

An embodiment of the present Invention will now be described by way of example, with reference to the accompanying figures in which.

DETAILED DESCRIPTION OF THE EMBODIMENTS

The present invention is predicated upon the movement of the leaves of an MLC. In one particular arrangement, where the MLC leaves are capable of travelling across the entire width of the aperture formed by the primary collimator edge, we have recognised that it is not necessary to have a collimator block which extends across the aperture for the entirety of its length (i.e. in the direction parallel to the direction of movement of the collimator block—"the movement direction"), because the main source of radiation leakage (the attenuation of which is a main objective of the collimator block) is not between the sides of the leaves but rather through the "gap" between opposing leaf tips. When the leaf tips are outside of the beam of radiation (i.e. extended fully across the aperture, so that the "gap" between the leaf tips is within the penumbra of the primary collimator edge and hence shielded from the radiation source) there is no radiation leakage as such, and the collimator block is not required to attenuate any radiation leakage. Accordingly, the collimator block need only be deep enough in the movement direction to cover the leaf tips while they move across the beam towards the primary collimator edge. Assuming that the leaves move from the centre of the aperture, between the two primary collimator edges, a concave V-shape can be provided (or cut) into the rear edge of the collimator block in such a way that the edge of this V-shape matches the trajectory the MLC leaves will take as the MLC leaves move and as the collimator block moves transversely thereto, and taking account of the speeds of movement of the MLC leaves and of the collimator block—which may be their maximum speeds, and/or may take account of their acceleration and/or deceleration. Depending on which side of the V the MLC leaves were last used, and on which side they are next to be used, a control system can determine which primary collimator edge the leaves next travel to.

Figure 1:
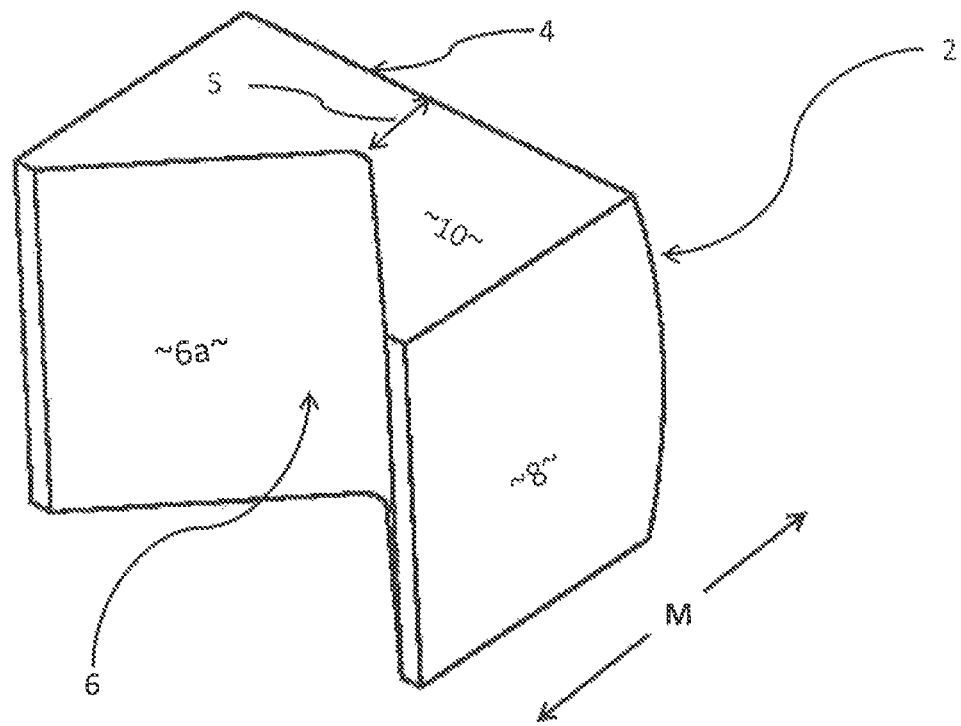
FIG. 1 is an isometric view of one embodiment of a collimator in accordance with the invention.

FIG. 1 is an isometric schematic view of one embodiment of a collimator block 2 which has a leading or front face 4, a main rear face 6 In the form of a V-shaped concave cut out formed by two substantially planar faces (only one, 6*a* being visible in the drawing). The collimator has two substantially planar side faces (only one 8*a* being visible in the drawing), and substantially planar faces to the top 10 and bottom (not visible). The collimator is moved in use in the direction of the arrows M. The distance S in the direction M between the front face 4 and the apex of the V-shape provides a safety margin, as will be described below. Note that FIG. 1 shows two small rear surfaces either side of the V-shaped cut-out; such an arrangement, provided the width (parallel to the front face 4 and transverse to the M axis) of these surfaces forms only a minor proportion of the entire width of the block 2, is within the scope of the claims, and the word "main" should be interpreted accordingly.

Figure 2:
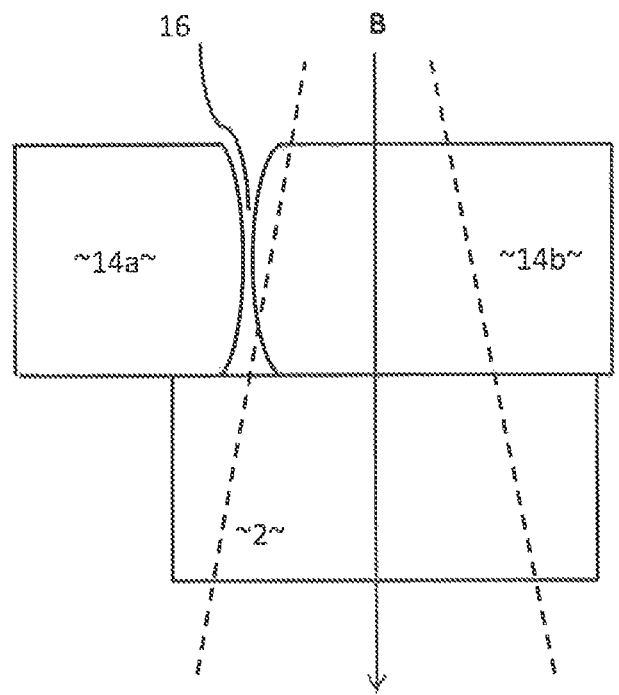
FIG. 2 is a side view of the collimator of FIG. 1 underlying the leaves of a multi-leaf collimator and showing the radiation beam produced by a source of radiation.

FIG. 2 is a side view, showing the collimator block 2 beneath the opposed leaves 14*a*, 14*b* of a multi-leaf collimator, with a gap 16 between the tips of the opposed leaves; with reference to direction M in FIG. 1, in FIG. 2 the direction M is perpendicular to the plane of the drawing. The MLC leaves are movable to left or right in FIG. 2. Radiation beam B (produced by a linear accelerator, for example) is shaped by a primary collimator (not shown) so as to have the outline shown by the dotted lines. As shown in FIG. 2, the MLC leaves are fully withdrawn to one side of the radiation beam B, so that the gap is outside the beam B and therefore the MLC and collimator 2 in combination provide full shielding of the radiation.

Figure 3:
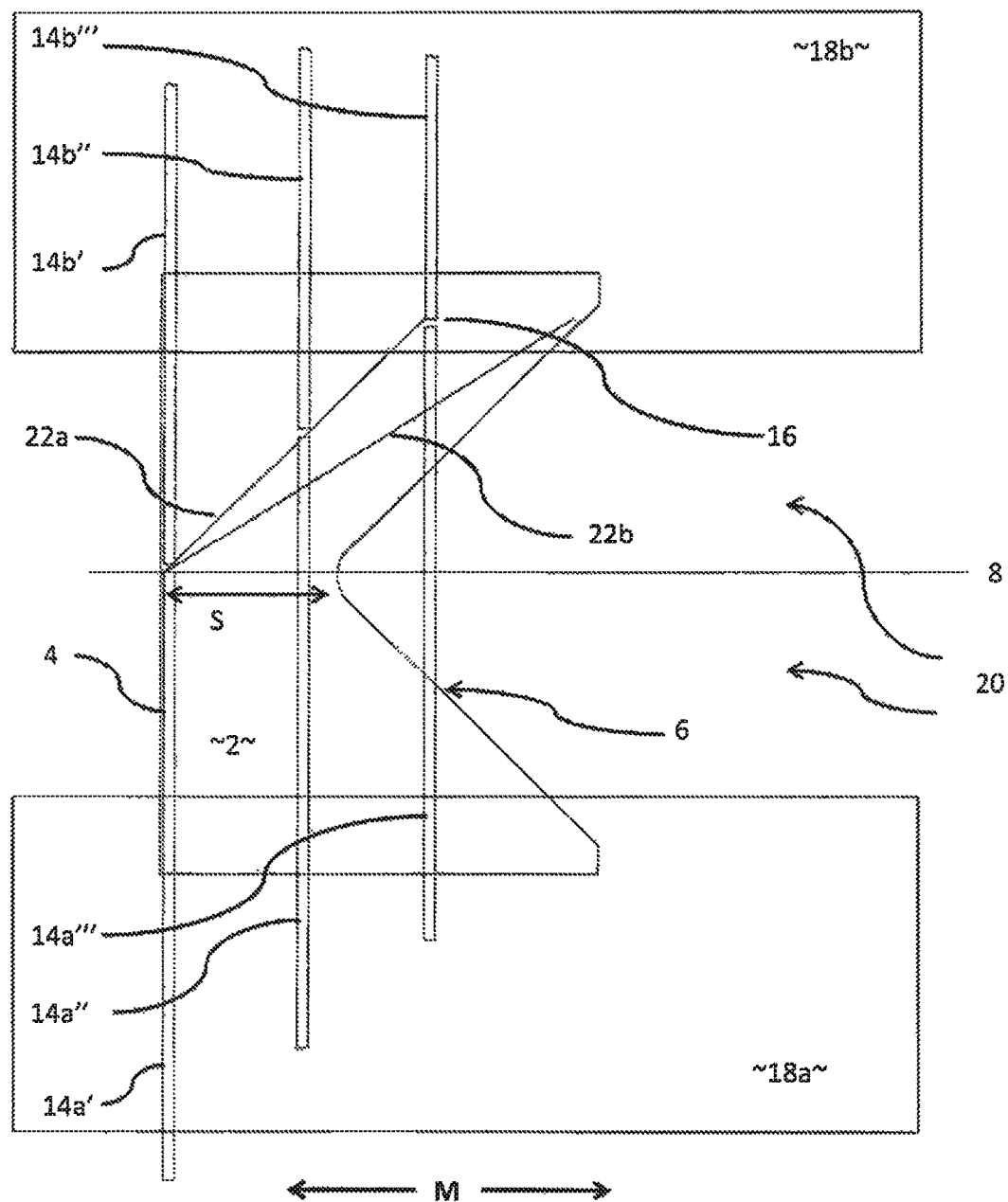
FIG. 3 is a schematic view illustrating how movement of the embodiment of FIG. 1 is controlled so as to match the trajectory of the gap between opposing leaves of a multi-leaf collimator, and FIGS. 4*a* and *b* are schematic top views of first and second embodiments of collimators in accordance with the invention.

Referring now to FIG. 3, this top view shows successive positions of the MLC leaves 14*a'*, 14*a"*, 14*a'''*, 14*b'*, 14*b"*, 14*b'''* as the MLC leaves move from the centre line 20 towards one side of the radiation aperture 20 created by the primary collimator (the aperture being illustrated between areas 18*a*, 18*b*, in which areas the radiation is fully shielded by the primary collimator (not shown)). As the MLC leaves move, so does the gap 16 between their tips; combining this movement with simultaneous movement of the collimator block 2, line 22*a* shows as a single vector line the trajectory of the gap 16 relative to the rear face 6 of the collimator block 2, where the angle of the rear face 6 is sufficient to ensure full shielding (i.e. to ensure that the collimator block 2 shields radiation which might pass through the gap 16). Line 22*a* is drawn in the case where the speed of movement of the MLC leaves 14*a*, 14*b* is approximately the same as that of the collimator block 2, so that line 22*a* is at an angle of at about 45 degrees to centre line 20 (which corresponds to the angle of the rear face 6 to the direction M). Line 22*b* illustrates the case where the MLC speed is somewhat slower, so that the angle to the centre line 20, and thus the angle of the rear face 6 to direction M, is decreased. Those skilled in the art will readily understand the geometries suitable for different types of MLC and collimator block movement apparatus. In most commercially available MLC/collimator arrangements, angles between 10 and 80 degrees would be feasible, and angles between 30 and 60 degrees represent a good compromise between the movement capabilities of the apparatus and enabling a significant reduction in weight of the collimator block.

It will be appreciated that the above arrangements assume a constant speed of movement of the MLC leaves and of the collimator block. Of course, in practice these elements are normally made of a dense material such as tungsten, which have considerable inertia, and therefore in practice the apparatus must accommodate the necessary acceleration and deceleration of the elements. This could be provided by a suitably programmed controller to control movement of the MLC leaves and/or collimator block appropriately, however the simple approach of providing a length S of collimator block 2 between the leading, front face 4 and the rear face 6 provides a suitable safety margin, thus ensuring that inertial effects do not allow the gap 16 to be unshielded whilst it moves towards a "parked" position, behind the penumbra 18b of the primary collimator. The same applies in the case where the MLC leaves are moving in the opposite direction, towards the penumbra 18a.

Figure 4A:
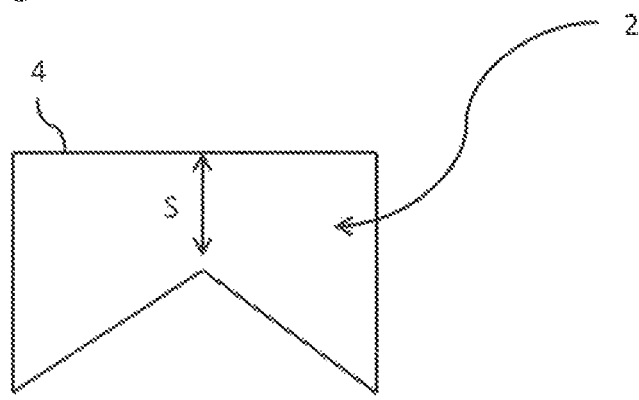
Figure 4B:
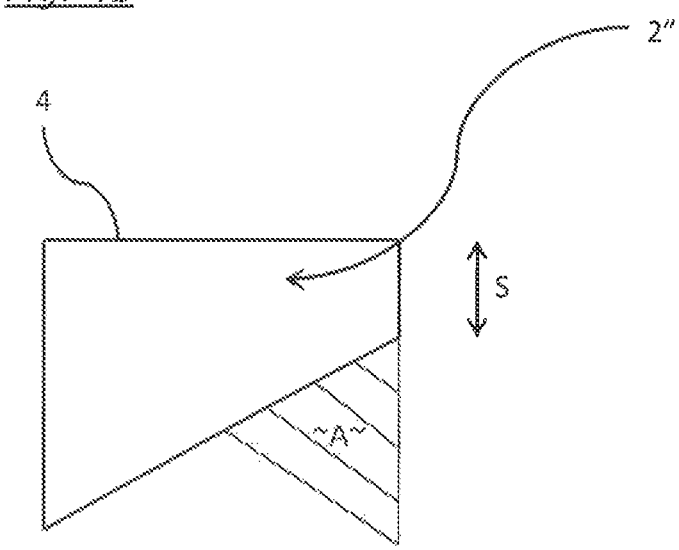

Referring now to FIG. 4, FIG. 4a shows in plan view the collimator block 2 of FIGS. 1 to 3 (but without two small rear surfaces either side of the V-shaped cut-out in FIG. 1); as explained above, this V-shaped collimator block corresponds to the case where the MLC leaves move from the centre line 20 of the radiation beam to one side of the aperture 20. It is also possible for the MLC leaves to move from one side of the aperture 20 to the other. In this case it will be appreciated that the shape of the collimator block 2" can be simpler, namely a "wedge" as shown in FIG. 4b. The collimator block 2" of FIG. 4b is provided with the same safety margin S as in the previous embodiment, however the movement speeds are adjusted to provide the same overall length of collimator block 2" (in the M direction) as was the case with the previous embodiment—meaning that there is a significant saving of material, and hence weight, compared to the first embodiment, as indicated by the shaded area A in FIG. 4b.

It will of course be understood that many variations may be made to the above-described embodiment without departing from the scope of the present invention. For example, although shown as symmetrical in FIG. 4a, the two main rear faces could be of different lengths so as to accommodate different speeds of movement of MLC leaves in different directions, and the apex of the V-shape could be central, as shown, or it could be offset to one or other side. Where there are more than two main rear faces, these will as before define a concave depression in the rear surface of the block, these rear faces may be arranged symmetrically or asymmetrically. As previously mentioned, it may be advantageous in some applications for the depth of the collimator block (i.e. into the plane of FIG. 4) to vary, such as by making the leading edge (adjacent the front face 4) thicker, or by profiling the block between its leading and trailing edges as described in EP2153448A1. Additionally or alternatively, the block may have a web of material, of lesser thickness than the remainder of the block, which is disposed against the rear face(s) so as to fit into the V-shaped space in the first embodiment or to render its appearance in FIG. 4a, or the appearance of the second embodiment in FIG. 4b, substantially rectangular. This web may be of the same material as the remainder of the block, and may be integral with it, and is useful for capturing any stray or scattered radiation; it may be disposed at any position vertically on the block (i.e. as shown in the vertical direction in FIG. 1. Where different variations or alternative arrangements are described above, it should be understood that embodiments of the invention may incorporate such variations and/or alternatives in any suitable combination.

The invention claimed is:

1. A multi-leaf collimator for a radiotherapy apparatus configured to emit a beam of therapeutic radiation, the multi-leaf collimator comprising:
    a plurality of leaves moveable across an aperture through which the beam passes;
    a block of radiation-attenuating material for moving into and out of the beam of therapeutic radiation across the aperture in a direction transverse to the movement of the leaves, the block having:
        a top face and a bottom face, each transverse to a propagation direction of the beam and defining a depth direction extending from the top face to the bottom face;
        a front face defining a leading edge for when the block is moved into the beam;
        at least one main rear face, wherein the at least one main rear face is non-parallel to the front face;
        at least two side faces, each side face extending between the top face and the bottom face, the side faces extending between the front face and the at least one main rear face; and
        a first material disposed against the at least one main rear face.

2. The collimator according to claim 1, wherein the first material is the same radiation-attenuating material.

3. The collimator according to claim 1, wherein the first material is different from the radiation-attenuating material.

4. The collimator according to claim 1, wherein the first material is integral with the block.

5. The collimator according to claim 1, wherein the first material has a lesser thickness than the block.

6. The collimator according to claim 1, wherein the at least one main rear face is substantially planar in the depth direction of the block.

7. The collimator according to claim 1, wherein the block has a non-uniform thickness in the depth direction.

8. The collimator according to claim 1, wherein the at least one main rear face comprises two main rear faces forming a concave V-shape transverse to the propagation direction of the beam, in which each face of the V-shape rear face is nonparallel to the front face.

9. The collimator according to claim 8, wherein the first material is disposed between the two main rear faces forming a concave V-shape, and the material has a lesser thickness than the block.

10. The collimator according to claim 1, wherein at least one of the leaves or the block is configured to move such that a profile of the at least one of the leaves matches a profile of the rear face of the block extending in the direction of the beam.

11. The collimator according to claim 10, wherein the side faces are substantially planar or parallel to each other.

12. The collimator according to claim 10, wherein the at least one main rear face comprises a single main rear face extending between the two side faces.

13. The collimator according to claim 1, wherein at least one of the top face and bottom face are substantially planar.

14. The collimator according to claim 13, wherein the top face and bottom face are parallel to each other.

15. The collimator according to claim 1, wherein the collimator is arranged to be mountable in a radiotherapy apparatus so as to be moveable back and forth in a direction transverse to the front face.

16. The collimator of claim 1, wherein the block has a minimum thickness in a direction defined from the front face to the at least one main rear face, the minimum thickness being determined based on a speed of movement of the collimator.

17. A method of operating a radiotherapy apparatus, the radiotherapy apparatus including a multi-leaf collimator with leaves moveable across an aperture through which a radiation beam is emitted, and a block collimator moveable across the aperture in a direction transverse to the movement of the leaves, the method comprising:
   controlling movement of the leaves or the block collimator so as to match the leaves to a profile of a rear face of the block collimator extending in the direction of the radiation beam, the block collimator having:
   a top face and a bottom face, each transverse to a propagation direction of the beam and defining a depth direction extending from the top face to the bottom face;
   a front face defining a leading edge;
   at least one main rear face; and
   a first material disposed against the at least one main rear face.

18. The method according to claim 17, wherein controlling movement of the leaves or the block collimator includes accounting for acceleration or deceleration of the moving leaves or block collimator.

19. The block collimator according to claim 17, wherein the first material is integral with the block collimator.

* * * * *